United States Patent

Bigg et al.

[11] Patent Number: 5,633,255
[45] Date of Patent: May 27, 1997

[54] 1,2-DIHYDRO-2-OXO-3-AMINOQUINOXALINE DERIVATIVES, THEIR PREPARATION AND THEIR THERAPEUTIC APPLICATION

[75] Inventors: Dennis Bigg; Jean-Francois Patoiseau, both of Castres; Jean-Marie Autin, Labruguiere; Jean-Pierre Tarayre, Valdurenque, all of France

[73] Assignee: Pierre Fabre Medicament, Boulogne, France

[21] Appl. No.: 411,594
[22] PCT Filed: Oct. 7, 1993
[86] PCT No.: PCT/FR93/00991
§ 371 Date: Apr. 6, 1995
§ 102(e) Date: Apr. 6, 1995
[87] PCT Pub. No.: WO94/07870
PCT Pub. Date: Apr. 14, 1994

[30] Foreign Application Priority Data

Oct. 7, 1992 [FR] France ................ 92 11878

[51] Int. Cl.⁶ .............. A61K 31/495; C07D 241/44
[52] U.S. Cl. .............................. 514/255; 544/354
[58] Field of Search ..................... 544/354; 514/255

[56] References Cited

U.S. PATENT DOCUMENTS

| 3,446,809 | 5/1969 | Harris | 544/354 |
| 4,181,724 | 1/1980 | Hall | 424/250 |

FOREIGN PATENT DOCUMENTS

| 0008864 | 7/1979 | European Pat. Off. |
| 89.13961 | 10/1989 | France |

OTHER PUBLICATIONS

F.E. King and J.W. Clark–Lewis, J.Chem. Soc. 1953, 172–177.

H. Bredereck and W. Pfleiderer, Chem. Ber. 87, 1119–23 (1954).

E. Schipper and A.R. Day, J.Am. Chem. Soc. 73, 5672–5675 (1951).

J.W. Clark–Lewis, J.Chem. Soc., 1957, 422.

Abdulla et al., J. Heterocyclic Chem. 13, 427 (1976).

Sen et al., J. Indian Chem. Soc. 38, No. 4, 225–228 (1961).

Clark–Lewis, The Chemical Society, 1951, 422–430.

Tennant, The Chemical Society, 1963, 2428–2433.

J. Clark–Lewis "Quinoxaline Derivatives, Part III", J. Chem. Soc., 78, 1957 pp. 422–430.

Primary Examiner—Matthew V. Grumbling
Attorney, Agent, or Firm—The Firm of Gordon W. Hueschen

[57] ABSTRACT

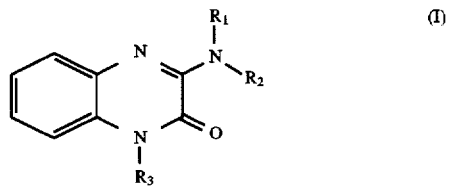

1,2-dihydro-2-oxo-3-amino-quinoxaline derivatives of general formula (I) in which $R_1$ and $R_2$ are independently hydrogen or a straight or branched $C_1$–$C_4$ alkyl radical, $R_3$ is a straight or branched $C_3$–$C_6$ alkyl, alkenyl or hydroxyalkyl grouping, their salts with pharmaceutically-acceptable acids, and a method for preparing them and their use in therapy are disclosed.

10 Claims, No Drawings

1,2-DIHYDRO-2-OXO-3-AMINOQUINOXALINE DERIVATIVES, THEIR PREPARATION AND THEIR THERAPEUTIC APPLICATION

This is a national stage application, filed under 35 USC 371, of PCT/FR93/00991, filed 07 Oct. 1993.

The present invention, produced at the Pierre Fabre Médicament Research Center, relates to novel chemical compounds, a process for their preparation and their application as medicaments.

Syntheses of 1,2-dihydro-2-oxoquinoxalines which are variously functionalized at position 3 are reported in the literature. Among these compounds, there may be noted esters (F. E. King and J. W. Clark-Lewis, J. Chem. Soc. 1953, 172–177), amides (H. Bredereck and W. Pfleiderer, Chem. Ber., 87, 1119–23 (1954) or amines. In this category, E. Schipper and A. R. Day describe the synthesis of 1,2-dihydro-3-amino-2-oxoquinoxaline (J. Am. Chem. Soc., 73, 5672–5675 (1951)) and J. W. Clark-Lewis describes that of 1,2-dihydro-3-aminomethyl-1-methyl-2-oxoquinoxaline (J. Chem. Soc. 1957, 422). Moreover, the presence at position 3 of a carbon chain, which may or may not be functionalized, imparts a bronchodilatory activity to the molecules, which is claimed in the following patents:

U.S. Pat. No. 4,181,724 of 1.1.80, Appl. 940,815 of 11.9.78 (Upjohn Co.).

Application FR 89.13961 of 23.10.89 (Pierre Fabre Médicament).

The present invention relates to the compounds of general formula I

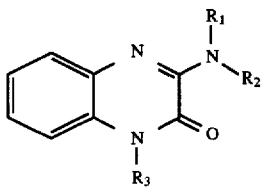

in which $R_1$ and $R_2$ represent, independently of each other, hydrogen or a linear or branched $C_1$–$C_4$ alkyl radical, $R_3$ represents a linear or branched $C_3$–$C_6$ alkyl, alkenyl or hydroxyalkyl group.

In addition, the invention covers the salts of the compounds of general formula I with pharmaceutically acceptable acids in the case of compounds which are sufficiently basic.

The compounds of general formula I of the invention may be prepared according to the following reaction scheme:

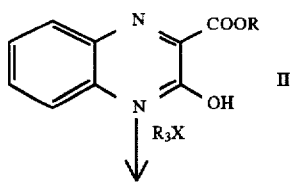

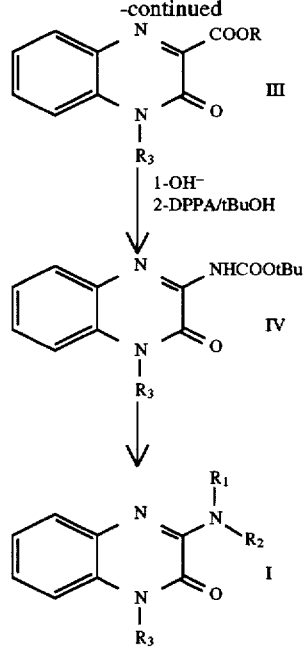

The starting compounds of general formula II in which R represents methyl or ethyl may be obtained according to known methods, for example those described by Abdulla et al., J. Heterocyclic Chem., 13, 427 (1976) or by Sen et al., J. Indian Chem. Soc., Vol. 38, No. 4, 1961, p. 225–228. The hydroxy ester II is treated with a reactant $R_3X$ in which $R_3$ has the same meaning as above and X represents a nucleofugal group such as the iodine, chlorine or bromine atom or a mesylate or tosylate group. The reaction may be carried out in the presence of a base such as sodium hydride, in a polar aprotic solvent such as DMF. It may also be performed in a medium such as $K_2CO_3$-acetone. After saponification with sodium hydroxide or with potassium hydroxide in an alcoholic medium, the compound III obtained, for which R represents a hydrogen atom, is treated with diphenylphosphoryl azide in tert-butanol in the presence of a base such as triethylamine. The reaction is preferably carried out at a temperature between 50° C. and the boiling point of tert-butanol to give, via the non-isolated intermediate isocyanate, the compound IV.

Compound IV is treated
either with a compound $R_1Y$, $R_1$ representing a linear or branched $C_1$–$C_4$ alkyl group and Y representing a labile group such as halogen (Cl, Br, I), mesylate or tosylate,
or with a $C_1$–$C_2$ dialkyl sulfate,
and then subjected to an acidic hydrolysis to give the compound I ($R_1 \neq H$, $R_2 = H$).

The alkylation reaction is advantageously carried out under phase transfer conditions using a water-immiscible solvent such as THF and a phase transfer catalyst such as, by way of example, benzyltriethylammonium chloride. The acidic hydrolysis may be performed by treatment with alcoholic hydrochloric acid at a temperature between room temperature and the boiling point of the solvent, or with trifluoroacetic acid at room temperature. The same compound IV is subjected directly to acidic hydrolysis to yield the compound I in which $R_1 = R_2 = H$.

The compounds of general formula I for which $R_1$ and/or $R_2$ represent hydrogen may be alkylated according to the standard methods used to alkylate primary or secondary amines such as, by way of example, treatment with a $C_1$–$C_4$ alkyl halide, to give the compounds I in which $R_1$ and $R_2 \neq H$.

The examples below illustrate the invention without, however, limiting the scope thereof.

The microanalyses and the infrared and NMR spectra confirm the structure of the compounds obtained.

EXAMPLE 1

1) 3-Ethyl 1-n-propyl-1,2-dihydro-2-oxoquinoxalinecarboxylate 1.

To a suspension of 18.25 g (0.084 mol) of 3-ethyl 2-hydroxyquinoxaline carboxylate in 300 ml of acetone are added 11.55 g (0.084 mol) of potassium carbonate and 22.8 ml of n-propyl bromide, and the whole mixture is heated at reflux for 7 hours. After evaporation of the solvent under vacuum, the residual mass is extracted with ethyl ether. The inorganic salts are then filtered off and the filtrate is evaporated under vacuum. The brown oil thus obtained is purified on a column of silica. Elution with a 30/70 ethyl acetate/hexane mixture gives, after evaporation, 14.6 g (yield 58%) of compound 1 in the form of yellow crystals (m.p.=65° C.).

TLC: Rf=0.35 (30/70 ethyl acetate/hexane).

2) 1-n-propyl-1,2-dihydro-2-oxoquinoxaline-3-carboxylic acid 2.

A solution of 14.6 g of ester 1 (0.056 mol) in 50 ml of 95° ethanol and 56 ml of 2N sodium hydroxide (0.112 mol) is stirred for 30 minutes at 50° C. After cooling and acidification by addition of 1N hydrochloric acid solution, the suspension obtained is chilled for one hour. The crystals are then filtered off, washed with water and with 95° ethanol and then dried under vacuum at 50° C. 12.24 g of acid 2 are thus recovered in the form of yellow flakes (yield 94%).

m.p.=172° C.

TLC=Rf=0.65 (50/50 methanol/chloroform).

3) 1-n-propyl-1,2-dihydro-2-oxo-3-tert-butoxycarbonylaminoquinoxaline 3.

A solution of 12.24 g (0.05227 mol) of the acid 2, 15.1 ml (0.11 mol) of triethylamine and 23.1 ml (0.105 mol) of diphenylphosphoryl azide in 350 ml of tert-butanol is heated at reflux for 5 hours. After evaporation of the solvent, the residual oil is taken up in sodium bicarbonate solution and extracted with ethyl acetate.

The organic phase is washed with water and then with brine, followed by drying over sodium sulfate and concentration under vacuum. The solid obtained is triturated in ethyl ether, filtered, washed and dried to give 12 g of white needles of compound 3 (yield 75%).

m.p.=126°-127° C.

TLC=Rf: 0.61 (30/70 ethyl acetate/hexane).

4) 1-n-propyl-1,2-dihydro-2-oxo-3-aminoquinoxaline 4.

A solution of 7.12 grams (0.0234 mol) of carbamate 3 in 50 ml of methanol and 35 ml of 6N hydrochloric acid is stirred at room temperature for 4 hours. The solution is neutralized, with cooling, by addition of 6N sodium hydroxide. The crystals formed are filtered off, washed with water and dried at 50° C. 4.55 g (yield 95%) of compound 4 are thus obtained in the form of a white powder.

m.p.=191°-192° C.

TLC=Rf: 0.65 (50/50 ethyl acetate/hexane).

5) 1-n-propyl-1,2-dihydro-2-oxo-3-aminoquinoxaline hydrochloride 5.

The crystals of compound 4 obtained above are suspended in ethanol. An ethanolic solution of hydrogen chloride gas is then added: the base dissolves and the hydrochloride then begins to precipitate out. After cooling and dilution with ethyl ether, the crystals are filtered off and then washed with a 50/50 ethanol/ethyl ether mixture, and then with ethyl ether. After drying, 4.25 g (yield 80%) of compound 5 are recovered in the form of white crystals.

m.p.=188° C. (sublimation).

TLC=Rf: 0.65 (50/50 ethyl acetate/hexane).

EXAMPLE 2

1-n-propyl-1,2-dihydro-2-oxo-3-methylaminoquinoxaline hydrochloride 6

A solution of 9.32 g (0.03 mol) of carbonate 3 in 100 ml of tetrahydrofuran is stirred at room temperature for 24 hours in the presence of 3.4 ml of methyl sulfate, 21 ml of 6N sodium hydroxide and 684 mg of benzyltriethylammonium chloride.

After evaporation of the solvent, the residue is taken up in water and extracted with ethyl acetate. After washing with water, drying over sodium sulfate and evaporation under vacuum, the oil recovered (intermediate N-methyl carbamate) is treated with a solution of 50 ml of 6N hydrochloric acid for 2 hours at 60° C. This solution is then poured onto ice and neutralized by addition of 6N sodium hydroxide. The solid formed is extracted with ethyl acetate and the hydrochloride is isolated by working in an identical manner to the above example.

3.30 g (yield 65%) of compound 6 are thus recovered in the form of white crystals.

m.p.=150°-151° C.

TLC=Rf: 0.50 (30/70 ethyl acetate/hexane).

EXAMPLE 3

1-n-propyl-1,2-dihydro-2-oxo-3-dimethylaminoquinoxaline hydrochloride 7

2 g (0.009 mol) of compound 6 in 15 ml of N,N-dimethylacetamide are stirred for 1 hour at room temperature in the presence of 0.4 g of 60% sodium hydride. 1.54 ml (0.025 mol) of methyl iodide are then added and the mixture is heated at 60° C. for 1 hour.

After evaporation of the solvent under vacuum, the hydrochloride is obtained in the same manner as in the above examples.

1.79 g of white crystals of compound 7 are isolated (yield=75%).

m.p.=120°-121° C.

TLC=Rf: 0.30 (10/90 ethyl acetate/hexane).

EXAMPLE 4

1-phenyl-1,2-dihydro-2-oxo-3-aminoquinoxaline hydrochloride 14

A solution of 4 g of 1-phenyl-1,2-dihydro-2-oxo-3-tert-butoxycarbonylaminoquinoxaline (0.012 mol) in trifluoroacetic acid is left stirring for 30 minutes. After evaporation under vacuum, the residue is taken up in sodium bicarbonate solution and extracted with ethyl acetate. The organic phase is then washed with water, dried over sodium sulfate and concentrated.

After purification on silica gel, eluting with a 30/70 ethyl acetate/CHCl$_3$ mixture, and then after hydrochlorination in an identical manner to the above examples, 2.5 g of compound 14 are obtained in the form of white crystals (yield 78%).

m.p.=191° C.

TLC=Rf: 0.5 (50/50 ethyl acetate/hexane).

EXAMPLE 5

1-(3-methyl-3-hydroxy)butyl-1,2-dihydro-2-oxo-3-aminoquinoxaline hydrochloride 17.

A solution of 4 g of 1-phenyl-1,2-dihydro-2-oxo-3-tert-butoxycarbonylaminoquinoxaline (0.012 mol) in 30 ml of 6N hydrochloric acid is maintained at 80° C. for 2 hours with stirring.

After cooling, the solution is poured onto ice and neutralized with 6N sodium hydroxide. After filtration and washing with water, the solid formed is taken up in acetone and the solution is then dried over sodium sulfate and evaporated to dryness under vacuum. After hydrochlorination, 3 g of compound 17 are obtained (yield 93%) in the form of white crystals.

m.p.=190° C.

TLC=Rf: 0.25 (50/50 ethyl acetate/hexane).

Table I below summarizes the main products synthesized.

TABLE I

| Compounds | $R_1$ | $R_2$ | $R_3$ | Salt | m.p. (°C.) |
|---|---|---|---|---|---|
| 4 | H | H | $n.C_3H_7$ | base | 191–192 |
| 5 | H | H | $n.C_3H_7$ | HCl | 188 |
| 6 | $CH_3$ | H | $n.C_3H_7$ | HCl | 150–151 |
| 7 | $CH_3$ | $CH_3$ | $n.C_3H_7$ | HCl | 120–121 |
| 8 | H | H | $n.C_4H_9$ | HCl | 195 |
| 9 | $CH_3$ | H | $n.C_4H_9$ | HCl | 150 |
| 10 | $CH_3$ | $CH_3$ | $n.C_4H_9$ | HCl | 130 |
| 11 | H | H | $-CH_2-CH=CH_2$ | HCl | 191 |
| 12 | $CH_3$ | H | $-CH_2-CH=CH_2$ | HCl | 148 |
| 13 | $CH_3$ | $CH_3$ | $-CH_2-CH=CH_2$ | HCl | 145 |
| 14 | H | H | $-CH_2-CH=C(CH_3)_2$ | HCl | 191 |
| 15 | $CH_3$ | H | $-CH_2-CH=C(CH_3)_2$ | HCl | 177 |
| 16 | $CH_3$ | $CH_3$ | $-CH_2-CH=C(CH_3)_2$ | HCl | 130 |
| 17 | H | H | $-CH_2-CH_2-C(OH)(CH_3)_2$ | HCl | 190 |
| 18 | $CH_3$ | H | $-CH_2-CH_2-C(OH)(CH_3)_2$ | base | 90 |

BIOLOGICAL EXPERIMENTS

1—Pharmacological study

The compounds of the invention were subjected to pharmacological tests which revealed their value as broncholyric agents.

To this end, the compounds were studied for their antagonistic effect on the contractions induced by various products according to the following procedure.

A piece of trachea from a male three-colored guinea pig weighing 400 g on average is cut into rings and mounted (2.5 cm approximately) in an insulated organ tank which is thermostatted at 37° C. and filled with oxygenated Tyrode's solution. The isometric contractions induced by the various mediators are recorded using a Gould Statham UC2 sensor (Gould Inc. Oxnard, Calif., U.S.A.) or a Palmer Bioscience UF1 sensor connected to a potentiometric recorder (Linseiss, Selb, FRG).

At the start of the experiment, the fragment of trachea is subjected to a tension of 1 g and left to stand for 1 hour.

The following mediator concentrations are used (concentrations generally inducing a maximum contraction): histamine dihydrochloride, 10 µg/ml; potassium chloride, 1850 µg/ml. The concentrations of agents used result in contractions which become maximal after 5 to 15 min. depending on the mediators and remain at a steady level thereafter. A concentration of the product studied is administered for each contraction and the product is left in contact with the trachea for 5 min. The possible inhibition obtained after this time is measured (percentage of variation in the amplitude of the contraction). The trachea is next washed for 15 seconds and left to stand for 10 min. approximately (time necessary to return to the base tonus) before inducing a new contraction.

The water-insoluble products are diluted in 0.178% (v.v) (final bath concentration) dimethyl sulfoxide (DMSO). This DMSO concentration does not result in any effect with regard to the contractions of the various mediators studied.

The 50% inhibitory concentrations ($IC_{50}$) are calculated using an SAS (Statistical Analysis System) program based on the model of Bliss and Cattel (Bliss C. I. and Cattel McK. Biological Assay Ann. Rev. Physiol. 5, 479, 1943).

The results obtained with some compounds of the invention are given, by way of example, in Tables 2 and 3.

TABLE II

| ANTAGONISM OF THE EFFECT OF POTASSIUM CHLORIDE | |
|---|---|
| Compound No. | $IC_{50}$ (µg/ml) |
| 5 | 19.3 |
| 6 | 4.7 |
| 7 | 28 |
| 8 | 9.6 |
| 9 | 11.1 |
| 10 | 45 |
| 11 | 21 |
| 12 | 9.1 |
| 13 | 19.3 |
| 14 | 7.4 |
| 17 | 45 |
| Theophylline | 30 |

TABLE III

| ANTAGONISM OF THE EFFECT OF HISTAMINE | |
|---|---|
| Compound No. | $IC_{50}$ (µg/ml) |
| 5 | 4.6 |
| 6 | 6.4 |
| 7 | 10.7 |
| 8 | 1.7 |
| 9 | 0.55 |
| 10 | 5.7 |
| 11 | 5.9 |
| 12 | 1.1 |
| 13 | 8.6 |
| 14 | 2.6 |
| 15 | 0.65 |
| 16 | 13.5 |

TABLE III-continued

ANTAGONISM OF THE EFFECT OF HISTAMINE

| Compound No. | IC$_{50}$ (µg/ml) |
| --- | --- |
| 17 | 23 |
| Theophylline | 30 |

The compounds of the invention were also tested on the pleurisy model with Zymosan in rats (Tarayre et al. Pharmacol. Res., 21, 385, 1989) according to the following procedure:

Technique:

10 mg of Zymosan in a volume of 0.15 ml of sterile 0.9% NaCl are injected into the pleural cavity of male Sprague Dawley rats mildly anesthetized with ether. The animals are sacrificed 1 hour later and the pleural exudate is withdrawn and measured.

Treatment:

The animals are kept unfed from the evening before. The products are administered p.o. one hour before injection of the inflammation-inducing agent, at a dose of 100 mg/kg.

The results obtained are given in Table IV below.

TABLE IV

| Compound No. | Zymosan Pleurisy volume pleural exudate |
| --- | --- |
| 5 | −21% |
| 6 | −27% |
| 7 | −44% |
| 8 | +4% |
| 9 | −29% |
| 10 | −47% |
| 11 | −33% |
| 12 | −31% |
| 13 | −43% |
| 14 | −14% |
| 15 | −5% |

2—Therapeutic applications

The compounds of the invention are bronchodilators which may be used for treating diseases such as chronic obstructive bronchopneumopathies, respiratory insufficiency and emphysema.

The pharmaceutical compositions may be in an appropriate form for administration via the oral, rectal, parenteral or local route, for example in the form of wafer capsules, tablets, granules, gelatin capsules or drinkable suspensions, syrups or liquid solutions, sprayable aerosols or solutions, and may contain appropriate excipients.

The daily dose may range from 50 to 1000 mg.

We claim:

1. A 1,2-Dihydro-2-oxo-3-aminoquinoxaline compound selected from those of formula I

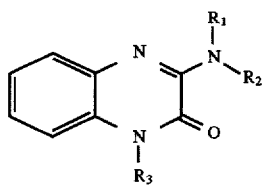

in which

R$_1$ and R$_2$ represent, independently of each other, hydrogen or a linear or branched C$_1$–C$_4$ alkyl radical, R$_3$ represents a linear or branched C$_3$–C$_6$ alkyl, C$_3$–C$_6$ alkenyl or C$_3$–C$_6$ hydroxyalkyl group, and a pharmaceutically, acceptable acid addition salt thereof.

2. A compound of claim 1, chosen from the group consisting of:

1-n-propyl-1,2-dihydro-2-oxo-3-aminoquinoxaline
1-n-propyl-1,2-dihydro-2-oxo-3-methylaminoquinoxaline
1-n-propyl-1,2-dihydro-2-oxo-3-dimethylaminoquinoxaline
1-n-butyl-1,2-dihydro-2-oxo-3-aminoquinoxaline
1-n-butyl-1,2-dihydro-2-oxo-3-methylaminoquinoxaline, and
1-n-butyl-1,2-dihydro-2-oxo-3-dimethylaminoquinoxaline
1-allyl-1,2-dihydro-2-oxo-3-aminoquinoxaline
1-allyl-1,2-dihydro-2-oxo-3-methylaminoquinoxaline
1-allyl-1,2-dihydro-2-oxo-3-dimethylaminoquinoxaline
1-prenyl-1,2-dihydro-2-oxo-3-methylaminoquinoxaline
1-prenyl-1,2-dihydro-2-oxo-3-dimethylaminoquinoxaline
1-(3-methyl-3-hydroxy)butyl-1,2-dihydro-2-oxo-3-aminoquinoxaline, and
1-(3-methyl-3-hydroxy)butyl-1,2-dihydro-2-oxo-3-methylaminoquinoxaline, in the form of the free base thereof or in the form of a therapeutically, acceptable salt.

3. A process for the preparation of a compound according to claim 1, comprising the following steps: a 1,2-dihydro-2-oxoquinoxaline-3-carboxylic acid derivative of formula III

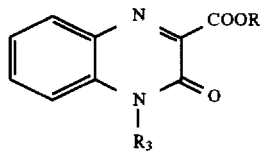

in which R represents a hydrogen atom and R$_3$ is C$_3$–C$_6$ alkyl, C$_3$–C$_6$ alkenyl, or C$_3$–C$_6$ hydroxyalkyl, is treated with diphenylphosphoryl azide in tert-butanol, the product formed is optionally alkylated, and hydrolyzed in an acidic medium, and the product obtained after hydrolysis is then optionally alkylated.

4. A process according to claim 3, characterized in that the reaction with diphenylphosphoryl azide in tert-butanol is carried out at a temperature between 50° C. and the boiling point of tert-butanol.

5. A process according to claim 3, characterized in that the alkylation reaction is carried out by the action of a reactant R$_1$Y, R$_1$ representing a linear or branched C$_1$–C$_4$ alkyl group, and Y representing a labile group selected from Cl, Br, I, mesylate, tosylate, and a C$_1$–C$_2$ dialkyl sulfate.

6. A process according to claim 5, wherein the akylation is performed under phase-transfer conditions using a two-phase medium consisting of a solvent, an aqueous phase, and a catalyst.

7. A process according to claim 3, characterized in that the acidic hydrolysis step is carried out in alcoholic hydrochloric acid at a temperature between room temperature and the boiling point of the solvent, or trifluoroacetic acid at room temperature.

8. The method of treating a mammal afflicted with a chronic obstructive bronchopneumopathy, respiratory insufficiency, or emphysema, comprising the step of administering to said mammal an effective amount of a compound of claim 1 or claim 2.

9. A pharmaceutical composition containing, as active principle, an effective amount of at least one compound according to claim 1 or claim 2, combined with a pharmacologically-acceptable pharmaceutical vehicle.

10. A process of claim 6, wherein the solvent is tetrahydrofuran, the aqueous phase is aqueous sodium or potassium hydroxide, and the catalyst is benzyltriethylammonium chloride.

* * * * *

UNITED STATES PATENT AND TRADEMARK OFFICE
CERTIFICATE OF CORRECTION

PATENT NO. : 5,633,255
DATED : May 27, 1997
INVENTOR(S) : Dennis Bigg et al.

It is certified that error appears in the above-indentified patent and that said Letters Patent is hereby corrected as shown below:

Column 1, line 9: Delete the letter "M" at the end of the line.

Column 1, line 10: Insert the letter -- M -- in the beginning of the line so that it reads -- Médicament --.

Column 1, line 32: Delete the letter "M" at the end of the line.

Column 1, line 33: Insert the letter -- M -- in the beginning of the line so that it reads -- Médicament --.

Column 5, line 60: "broncholyric" should read -- broncholytic --.

Column 8, line 6: Replace the comma "," with a dash -- - -- between "pharmaceutically" and "acceptable".

UNITED STATES PATENT AND TRADEMARK OFFICE
CERTIFICATE OF CORRECTION

PATENT NO. : 5,633,255
DATED : May 27, 1997
INVENTOR(S) : Dennis Bigg et al.

It is certified that error appears in the above-indentified patent and that said Letters Patent is hereby corrected as shown below:

Column 8, line 26: Replace the comma "," with a dash -- - -- between "therapeutically" and "acceptable".

Signed and Sealed this

Second Day of September, 1997

Attest:

BRUCE LEHMAN

Attesting Officer

Commissioner of Patents and Trademarks